(12) United States Patent
Wandke et al.

(10) Patent No.: US 9,038,645 B2
(45) Date of Patent: May 26, 2015

(54) METHOD FOR TREATING HUMAN OR ANIMAL HAIR AND APPARATUS FOR CARRYING OUT THE METHOD

(75) Inventors: Dirk Wandke, Heilbad Heiligenstadt (DE); Matthias Kopp, Gieboldehausen (DE); Karl-Otto Storck, Duderstadt (DE); Maximilian Segl, Duderstadt (DE); Leonhard Trutwig, Duderstadt (DE); Johannes Scharf, Bergisch-Gladbach (DE)

(73) Assignee: CINOGY GmbH, Duderstadt (DE)

( * ) Notice: Subject to any disclaimer, the term of this patent is extended or adjusted under 35 U.S.C. 154(b) by 0 days.

(21) Appl. No.: 13/983,329

(22) PCT Filed: Jan. 27, 2012

(86) PCT No.: PCT/DE2012/000091
§ 371 (c)(1),
(2), (4) Date: Aug. 2, 2013

(87) PCT Pub. No.: WO2012/103877
PCT Pub. Date: Aug. 9, 2012

(65) Prior Publication Data
US 2013/0306100 A1 Nov. 21, 2013

(30) Foreign Application Priority Data
Feb. 2, 2011 (DE) .......................... 10 2011 010 273

(51) Int. Cl.
| A45D 7/02 | (2006.01) |
| D06M 10/02 | (2006.01) |
| D06P 5/20 | (2006.01) |
| H05H 1/24 | (2006.01) |
| A61N 1/32 | (2006.01) |
| A61N 1/40 | (2006.01) |

(52) U.S. Cl.
CPC . *A45D 7/02* (2013.01); *A61N 1/322* (2013.01); *A61N 1/40* (2013.01); *D06M 10/02* (2013.01); *D06M 10/025* (2013.01); *D06P 5/20* (2013.01); *D06P 5/2011* (2013.01); *H05H 1/2406* (2013.01); *H05H 2001/2418* (2013.01)

(58) Field of Classification Search
CPC .......... A45D 7/02; A61N 1/322; A61N 1/40; D06M 10/02; D06M 10/025; D06P 5/20; D06P 5/204; H05H 1/2406; H05H 2001/2418
USPC .......................... 132/148, 223–232, 212, 219
See application file for complete search history.

(56) References Cited

U.S. PATENT DOCUMENTS

| 4,797,533 A * | 1/1989 | Santhouse et al. ............ 219/225 |
| 5,743,278 A * | 4/1998 | Ookura et al. ................ 132/210 |
| 2004/0000319 A1* | 1/2004 | Carballada et al. ........... 132/224 |
| 2005/0172979 A1* | 8/2005 | Saida et al. .................... 132/228 |
| 2010/0212683 A1 | 8/2010 | Mizuno |

FOREIGN PATENT DOCUMENTS

| AU | 2003204454 A1 | 12/2003 |
| DE | 602 25 240 T2 | 4/2009 |

(Continued)

*Primary Examiner* — Rachel Steitz
(74) *Attorney, Agent, or Firm* — Whitham Curtis Christofferson & Cook, PC

(57) ABSTRACT

In order to treat human or animal hair fixedly arranged on a sopport, hair is divided into strands. The divided strands are subjected to a dielectric plasma treatment by drawing an apparatus connected to a high voltage source (8) through the strands. The apparatus can be in the form of tongs or have a comb-like structure.

9 Claims, 12 Drawing Sheets

(56) References Cited

FOREIGN PATENT DOCUMENTS

| DE | 10 2009 045 498 | A1 | 4/2011 |
|---|---|---|---|
| EP | 0592979 | A1 | 4/1994 |
| EP | 1367172 | A2 | 12/2003 |
| EP | 1 387 901 | B1 | 10/2007 |

* cited by examiner

Electrode 1

Electrode 2

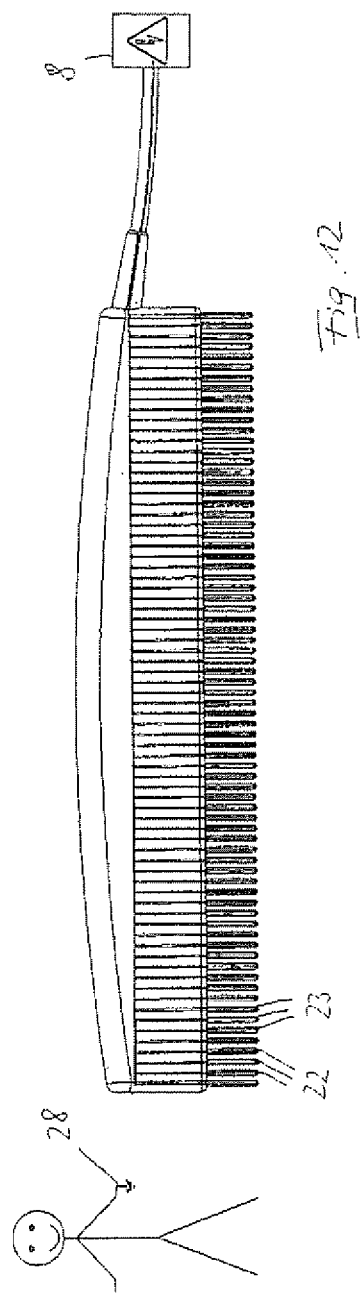

METHOD FOR TREATING HUMAN OR ANIMAL HAIR AND APPARATUS FOR CARRYING OUT THE METHOD

The invention relates to a method for treating human or animal hair which is fixedly arranged on a support.

The invention also relates to an apparatus for carrying out the method.

Numerous treatments for hair which is arranged such that it is fixed to a support are known. In this case, the support may be a suitable fabric of a wig or of a hairpiece, but also human or animal skin. When the hair is located on the associated human or animal body and is supported by the body, it can, in particular, grow and maintain its functional structure ("living hair"). Treatments for the hair include washing treatments by way of which the hair is freed of impurities and possibly disinfected. It is also known to color hair with chemical agents, to prepare hair for coloring or to change the structure of the hair such that it assumes a desired form, for example curls. Methods of this kind can be applied with the application of heat, but also at ambient temperature using chemical agents.

EP 0 592 979 A1 discloses modifying the surface of animal hair by a plasma treatment in order to make the hair more suitable for subsequent coloring. However, this hair is cut animal hair which is treated in a plasma chamber by a gas which can be excited to produce glow discharge by plasma. It goes without saying that a treatment of this kind is not suitable for hair which is fixedly arranged on a support, in particular for living hair which is still on the body.

The present invention is based on the object of enabling human or animal hair which is fixedly arranged on a support to be treated in order to improve the surface properties, in particular to prepare for a subsequent chemical treatment.

In order to solve this problem, provision is made, according to the invention, in a method of the abovementioned type to divide the hair into strands and to subject the divided strands to dielectric plasma treatment by drawing an apparatus which is connected to a high-voltage source through the strands.

The method according to the invention enables the treatment of un-cut human or animal hair by a dielectrically impeded plasma treatment. As a result, the advantages which can be achieved with a plasma treatment can be achieved in a simple manner in the case of hair which is fixedly arranged on the support, in particular in the case of living hair. These advantages can be found, in particular, in the increased absorption capability of the hair, for example for a dye, with a disinfecting action etc.

In a first embodiment of the method according to the invention, the divided strands are grasped between two flat electrodes which are arranged in the form of tongs and which are covered by means of in each case one dielectric in the direction of the strands. The electrodes are connected to a high-voltage source which is, in particular, a high-frequency AC-voltage source. The hair which is divided into strands is clamped between the two electrodes by the levers of the tongs being moved toward one another. In the state in which the two levers of the tongs are pressed lightly against one another, the apparatus is drawn along the length of the strands of hair, wherein the high-voltage field is present between the electrodes.

The flow of current is limited by the dielectrics which cover the electrodes in the direction of the strands, with the result that, for example, spark discharge cannot take place. Rather, the air which is present in the intermediate space between the dielectrics, in which the hair is located, is ionized there, with the result that the plasma is formed there. The surface of the hair which is drawn through between the electrodes which are covered by the dielectrics is modified by the plasma which is formed in this way. All the scalp hair of a human, for example, can be plasma-treated in strands in this way.

In one embodiment of the method according to the invention, the hair is divided into strands by means of a comb-like structure having tines which run parallel to one another, wherein the tines are formed with a conductive core which is surrounded on all sides by dielectric and are connected to a high-voltage source by the conductive core. In this case, the tines can jointly form an electrode of the high-voltage source, whereas the body which supports the hair, preferably close to the treated region of the hair, is connected to a reference potential, for example in the form of a counterelectrode. In this case, the hair, on account of its connection to the body, can itself form the counterelectrode for the active electrode, which is formed by the tines, of the high-voltage source. In this case, the counterelectrode is preferably connected to ground potential.

However, an arrangement in which the tines are individually alternately or in groups alternately connected to two different connections of a high-voltage source, with the result that different potentials are produced between adjacent tines, is preferred. In this case, the bunch of hair which is divided between the tines is subjected to a plasma treatment which takes place between the tines. The tines of the comb form parallel strands of hair which are therefore subjected to the plasma treatment in a simultaneous and parallel manner when the comb-like structure is drawn through the hair.

According to the invention, an apparatus for carrying out the method according to the above-mentioned first embodiment is characterized in that said apparatus is formed with a tongs-like apparatus body having two levers with which a divided strand of the hair can be grasped and can be guided between contact faces, which are situated opposite one another, of the levers, and in that the contact faces are formed by in each case one dielectric which in each case covers a flat electrode which can be connected to a high-voltage source and is arranged on one of the levers. In this case, the electrodes are preferably embedded in the dielectric, that is to say surrounded on all sides by the dielectric and routed out of the dielectric only with a current conduction means. In this case, the dielectrics form contact faces, which are of smooth design in one embodiment of the invention, whereas they are provided with raised portions and grooves in another embodiment of the invention, in order to subdivide a divided strand further into component strands in the longitudinal direction of the levers of the tongs-like housing body.

According to the invention, an apparatus for carrying out the method according to the abovementioned second embodiment is characterized in that it has a comb-like apparatus body having tines which run parallel to one another, in that the tines are formed with a conductive core which is surrounded on all sides by a dielectric, and in that the conductive cores are connected to a high-voltage source.

In this case, the dielectric which surrounds the tines is preferably in the form of a cohesive integral layer. Therefore, according to the invention, the plasma treatment of hair is performed by a comb-like structure being drawn through the hair or by a strand of hair being drawn between contact faces of two levers of a tongs-like apparatus, as is known, for example, for smoothing frizzy hair. The plasma treatment can therefore be performed with movements which are familiar to everyone, with the result that no new skills have to be learned in order to use the apparatuses according to the invention.

The frequencies used for the plasma treatment for the alternating high voltage are usually between 1 Hz and 100 MHz.

The action times of the plasma treatment depend on the field of use and can last from a few milliseconds, over several minutes, up to a few hours.

The high voltages can have a peak value of between 100 and 100,000 V. The applied voltage can be sinusoidal or pulsed (unipolar or bipolar). Plasma treatment with a DC voltage is also possible. It goes without saying that all voltage forms could be combined with one another.

The electrodes, in the form of the flat electrodes of the tongs-like apparatus body or in the form of the conductive cores of the tines, are composed of highly electrically conductive materials. If the high voltage is applied between the electrodes of the apparatus, the electrodes can be formed from identical materials. However, it is also feasible to use the support of the hair as a counterelectrode, wherein supports of the hair include, in particular, the human or animal body or the skin.

The distance between the tines of the comb-like structure can be between 0.1 and 5 mm. The same order of magnitude applies for the grooves which extend on the surface of the dielectric transverse to the longitudinal direction of the tongs-like structure.

The invention will be explained in greater detail below with reference to exemplary embodiments which are illustrated in the drawing, in which:

FIG. 12 shows a schematic illustration for a type of connection of the apparatus to the high-voltage source which is possible in all embodiments.

Figure 1:
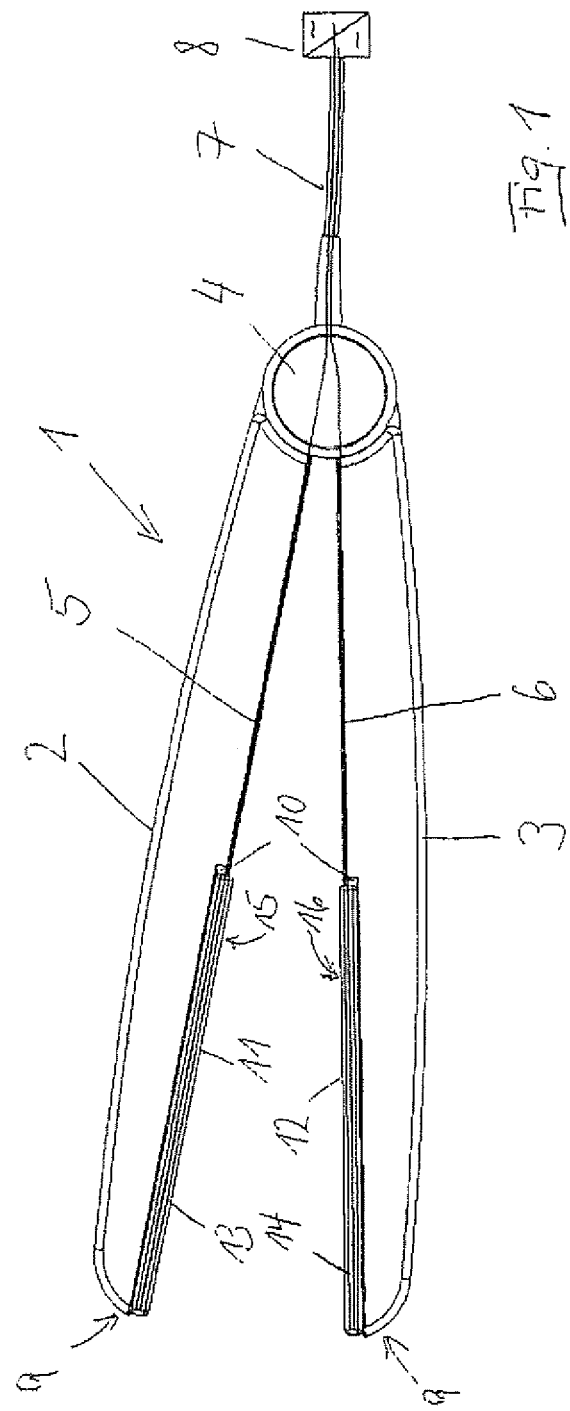
FIG. 1 shows a side view of an apparatus in a first embodiment which is in the form of tongs with two levers which are illustrated in the open state, wherein the feed line to in each case one electrode which is arranged on the two levers is shown.
Figure 2:
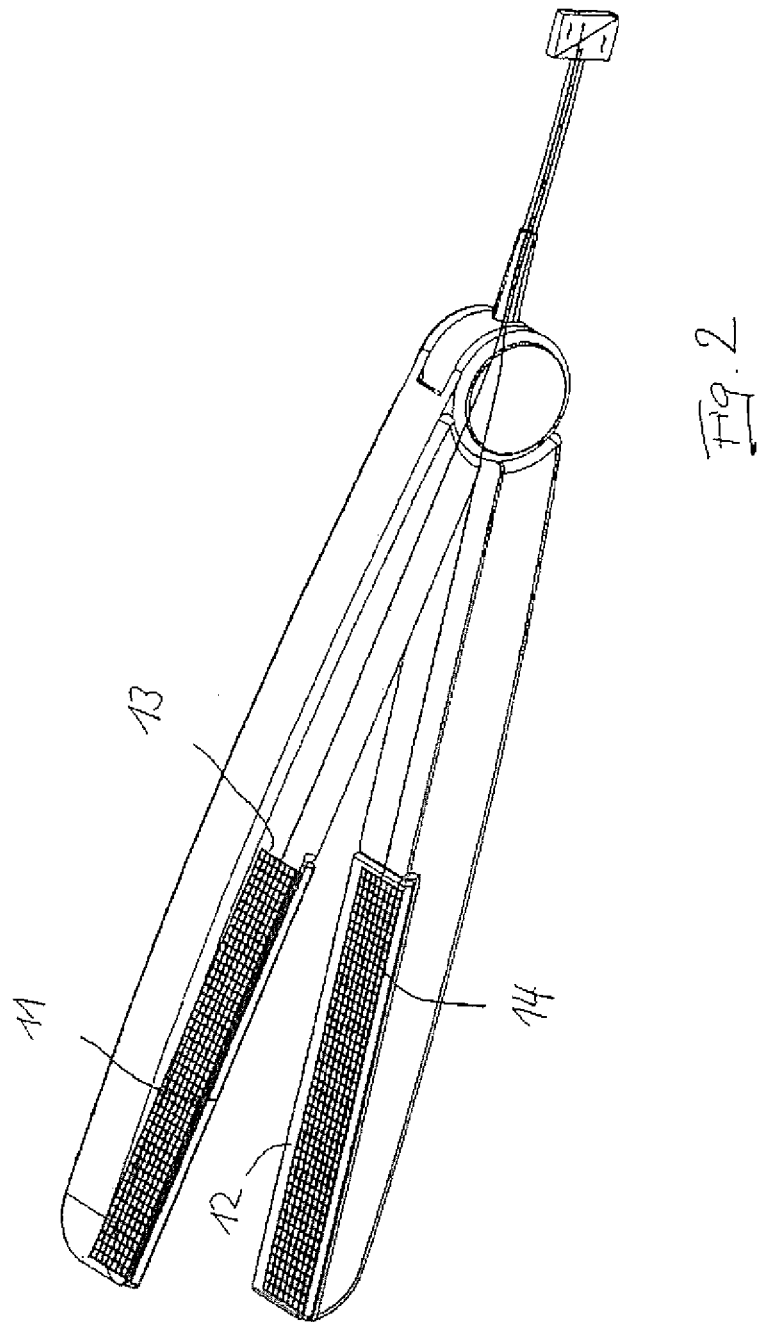
FIG. 2 shows a perspective illustration of the apparatus according to FIG. 1.
Figure 3:
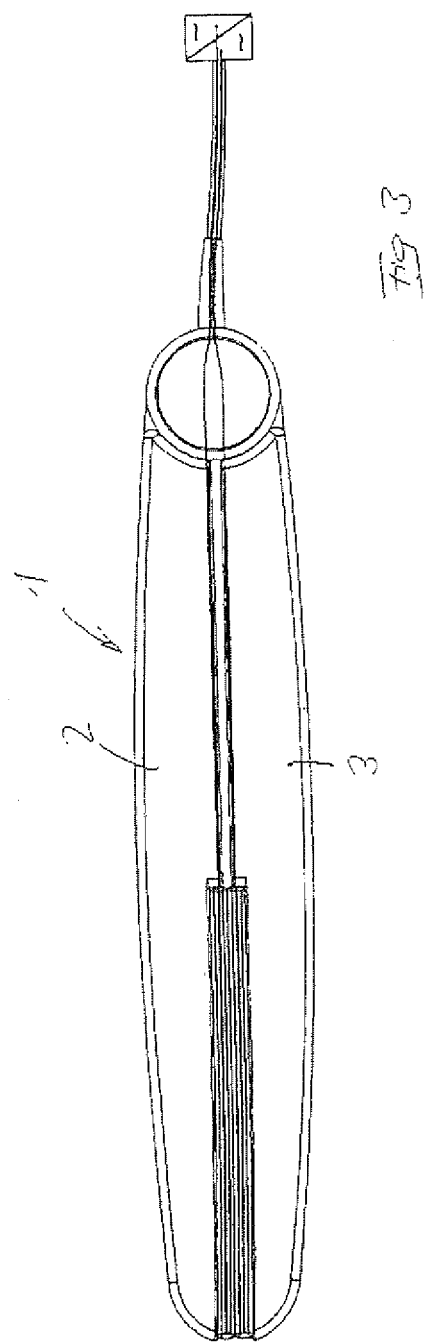
FIG. 3 shows a side view of the apparatus according to FIG. 1 in the closed state.

According to FIGS. 1 to 3, an apparatus comprises, in a first embodiment, a tongs-like apparatus body 1 which has two single-armed levers 2, 3 which are connected such that they can pivot in relation to one another at a common rotation axis 4, wherein the opening movement of the two levers 2, 3 in relation to one another is limited to the opening angle which is illustrated in FIGS. 1 and 2. The two levers 2, 3 are in the form of hollow housing parts which contain, in their interior, a current conduction means 5, 6 and are connected to a supply cable 7 of the apparatus. The supply cable 7 is connected to a high-voltage source 8.

The levers 2, 3—starting from their free ends 9—are provided approximately over half their length with in each case one recess 10 on the sides which face one another, in each case one dielectric 11, 12 being inserted into said recesses. The dielectric 11, 12 is composed of a non-conductive material, preferably of glass, ceramic or plastic with dielectric properties. In each case one electrode 13, 14 is embedded in the two dielectrics 11, 12. The electrode 30 is connected to the current conduction means 5 which runs in the same lever 2, whereas the electrode 14 is connected to the current conduction means 6. Since the electrodes 13, 14 are insulated from one another by the dielectrics 11, 12, a flow of current between the two electrodes 13, 14 is impeded.

The dielectrics 11, 12 have flat contact faces 15, 16 on the sides which face one another, the dielectrics bearing against one another in the closed state of the tongs-like apparatus body 1 (cf. FIG. 3) by way of said contact faces. In this case, the contact faces project out of the corresponding surfaces of the levers 2, 3 outside the recess 10 to a certain extent, with the result that the contact faces 15, 16 come into direct contact when the apparatus body 1 is closed.

Figure 4:
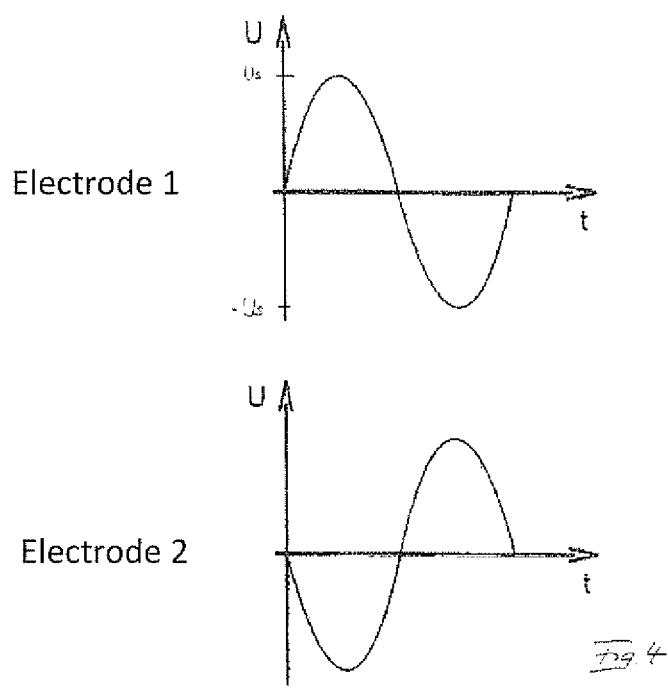
FIG. 4 shows an illustration, in the form of a graph, of the profiles of the high voltages which are supplied to the two electrodes.

In the embodiments illustrated in FIGS. 1 to 3, the two electrodes 13, 14 are connected to an AC-voltage connection of the high-voltage source 8. However, in this case, the two AC-voltage signals are phase-shifted through 180° in relation to one another, as is illustrated in FIG. 4 using sinusoidal high-voltage signals with a peak voltage Us. Therefore, a resulting AC voltage with a maximum voltage of 2 Us is produced between the electrodes 13, 14.

The peak voltages Us can be between 100 and 100,000 V. The voltage can be sinusoidal—as illustrated in FIG. 4, but pulsed (unipolar or bipolar) in the form of high-frequency pulses.

As illustrated in FIG. 2, the electrodes 13, 14 can be in the form of a lattice in a preferred embodiment, this being advantageous, in particular, when the electrodes 13, 14 are integrally cast in a thermoplastic or thermoset material as dielectric 11, 12 since the material can be distributed in liquid form through the lattice openings in the electrodes 13, 14 and therefore ensures that the electrodes 13, 14 are well embedded in the dielectrics 11, 12.

Figure 5:
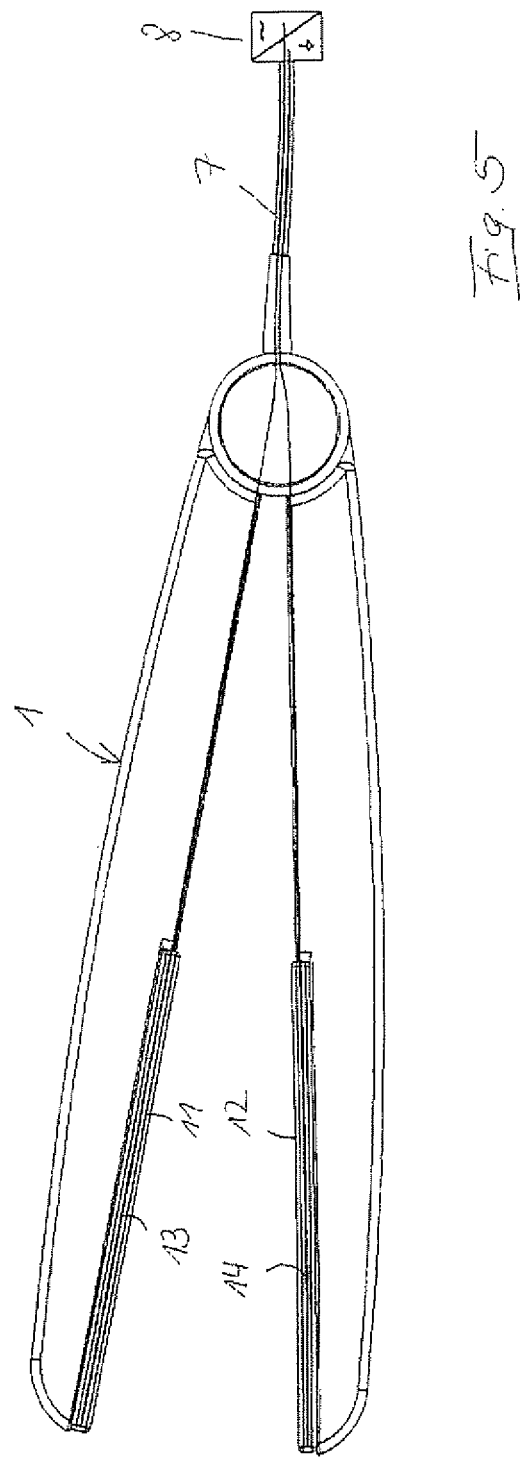
FIG. 5 shows a second embodiment of an apparatus according to the invention which corresponds to the apparatus according to FIG. 1, wherein only the electrodes are connected differently.

The exemplary embodiment illustrated in FIG. 5 corresponds to the exemplary embodiment according to FIGS. 1 to 3 in respect of the apparatus body 1 and the design of the electrodes 13, 14 and of the dielectrics 11, 12. However, in this case, the supply cable is connected to a high-voltage source 8 in such a way that one electrode 13 is connected to an AC voltage, whereas the other electrode 14 is connected to ground potential. There is therefore a change in potential with the maximum voltage Us or −Us between the two electrodes 13, 14 in this case.

During use, a divided strand, for example of human head hair, is placed between the contact faces 15, 15 of the levers 2, 3 and held between the levers 2, 3 which are pressed against one another. By pulling the apparatus body 1 away from the scalp of the person, the hairs of the strand of hair are drawn through the apparatus in the longitudinal direction, the electrodes 13, 14 of said apparatus in this case being connected to the connections of the high-voltage source 8. In this way, a plasma is formed between the dielectrics 11, 12 by ionized air, the hair between the dielectrics 11, 12 and the electrodes 13, 14 being treated by said plasma.

All the head hair of a person, for example, can be treated in succession by correspondingly separating numerous strands. However, it is also feasible to treat the hair only in strands which are spaced apart from one another in order to prepare for dyeing in streaks or to dye the hair in streaks, for example.

Figure 7:
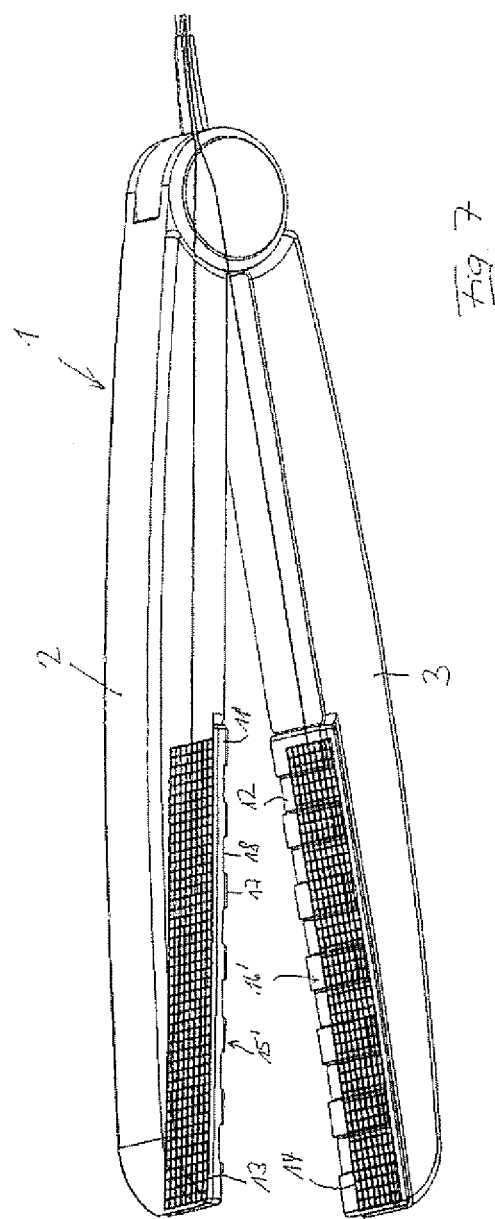
FIG. 7 shows a third exemplary embodiment of an apparatus of the type illustrated in FIG. 1, but wherein contact faces which face one another are provided with transverse grooves.
Figure 8:
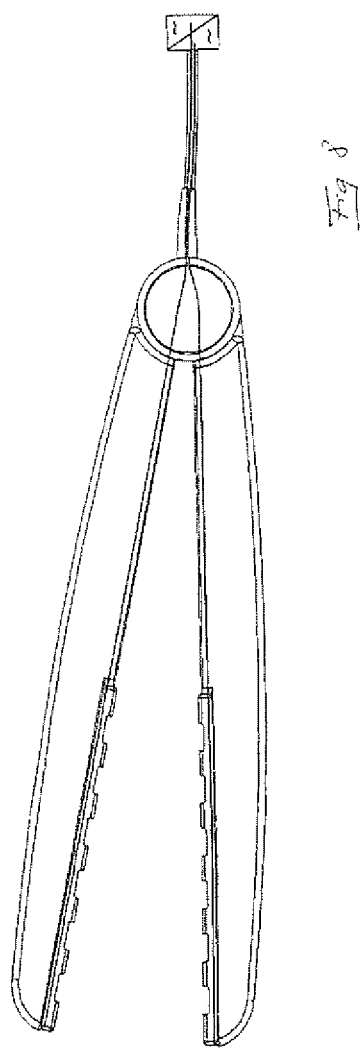
FIG. 8 shows a side view of the apparatus according to FIG. 7 in the open state.
Figure 9:
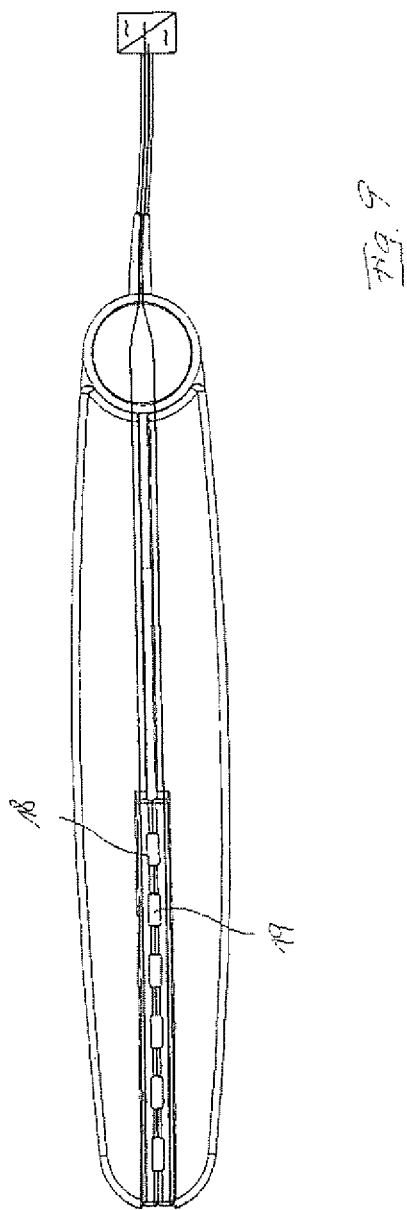
FIG. 9 shows a side view of the apparatus according to FIG. 7 in the closed state.

In the further embodiment of a treatment apparatus illustrated in FIGS. 7 to 9, the apparatus body 1 and the electrodes 13, 14 correspond to the embodiment of FIGS. 1 to 3 and, respectively, of FIG. 5. The only difference in this case is that the dielectrics 11, 12 have contact faces 15', 16' which are formed by alternately arranged projections 17 and grooves 18. In this case, the projections 17 and grooves 18 run transverse to the longitudinal direction of the levers 2, 3, with the result that the grooves 18 are oriented such that the hair can slide through the grooves 18 when the appliance is drawn away from the scalp of the person. The projections 17 can therefore further subdivide the divided strands of hair and thus make the plasma treatment more intense.

FIG. 9 shows that, in the closed state of the apparatus, transverse openings 19 are formed by the grooves 18, it being possible for bunches of hair which are divided by the strands to be drawn through said transverse openings.

Figure 6:
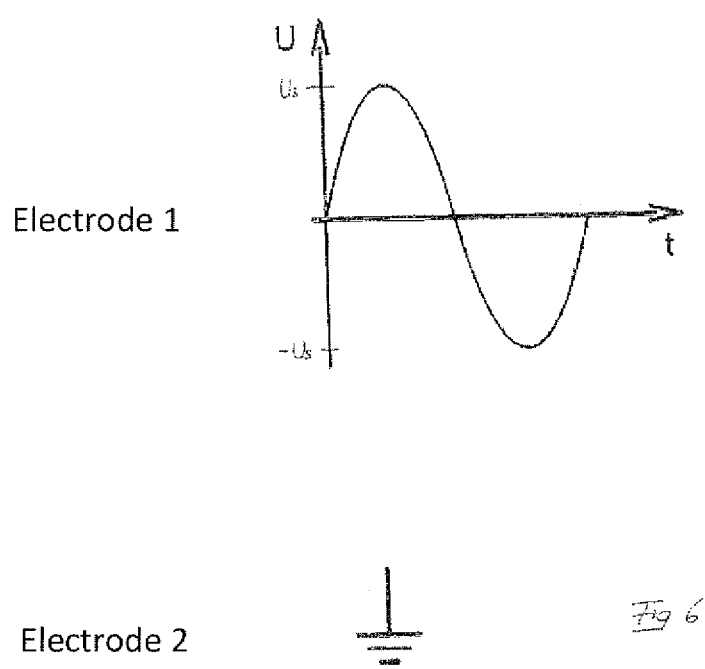
FIG. 6 shows an illustration, in the form of a graph, of the voltages which are supplied to the electrodes.

It can readily be seen that the apparatus according to FIGS. 7 to 9 can also be connected to the high-voltage source 8 according to FIG. 4 or else according to FIG. 6.

Figure 10:
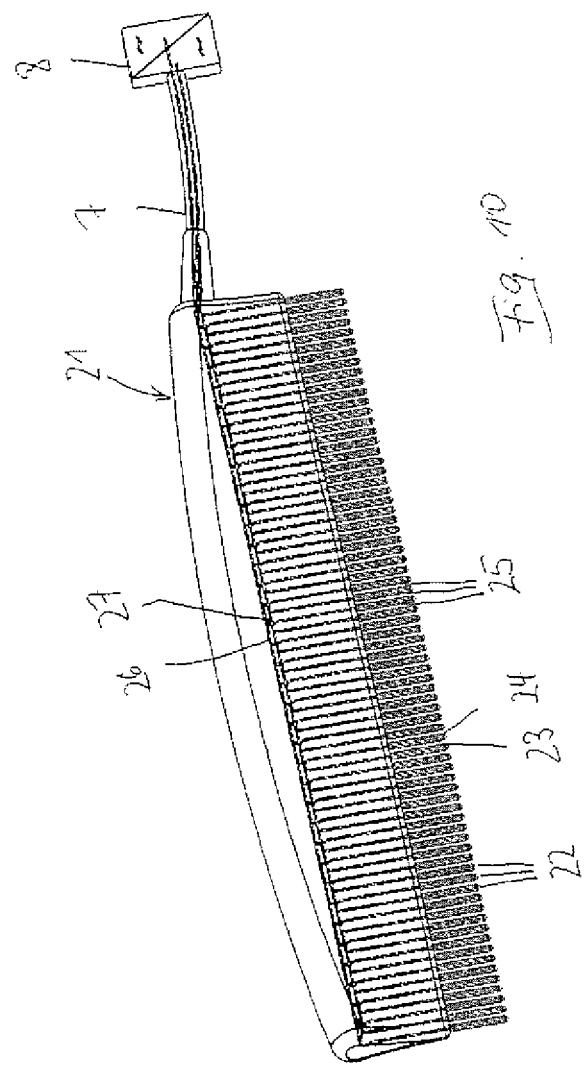
FIG. 10 shows a perspective illustration of an apparatus in an embodiment which is different in principle and has an apparatus body and comb-like tines which face one another in parallel, wherein the apparatus is supplied with voltage profiles according to FIG. 4.
Figure 11:
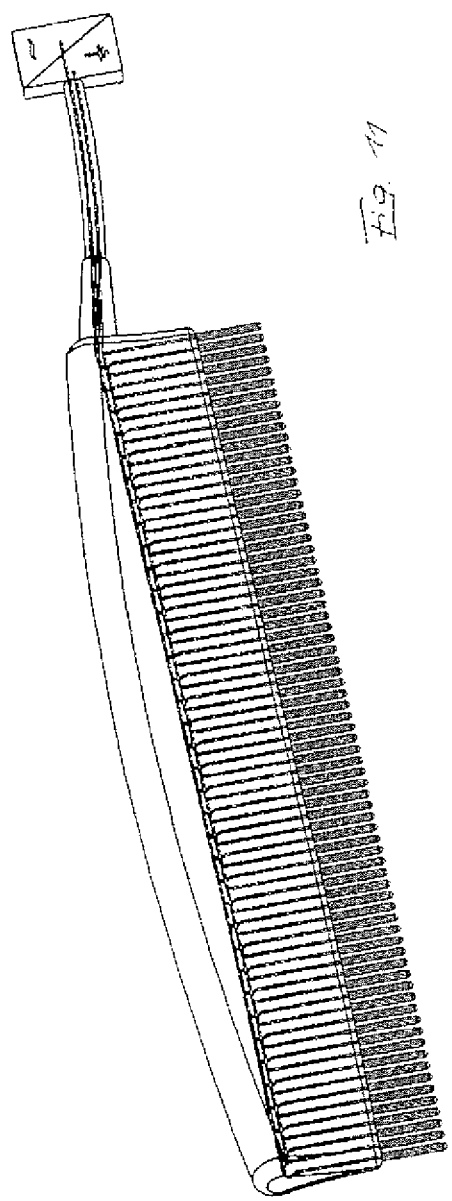
FIG. 11 shows an apparatus according to FIG. 10 which is operated with voltage profiles according to FIG. 6.

In the apparatus illustrated in FIGS. 10 and 11, the supply cable 7 of the high-voltage source 8 leads into a flat, elongate apparatus body 21 which has numerous tines 22 on its longitudinal side, said tines running parallel to one another and projecting out of the apparatus body 21 by a predetermined extent in each case. In the exemplary embodiment illustrated in FIGS. 4 and 5, the tines 22 all project out of the apparatus body 21 by the same length. Since the edge of the apparatus body 21, from which the tines 22 project, is rectilinear, a rectilinear line in which all the tines 22 end is therefore formed.

However, it is also possible to form a bent line, or a line which may be bent several times, with the free ends of the tines 22 by the tines 22 projecting out of a straight edge of the apparatus body 22 by different lengths, or by the edge of the apparatus body 21 itself being correspondingly curved.

The tines 22 in each case comprise a pin-like conductive core 23 which projects out of the apparatus body 21 and which is surrounded on all sides by a dielectric 24 as far as the housing body 21. Intermediate spaces 25, which correspond to a rough spacing between customary tine combs, are formed between the tines 22. When the apparatus with the tines 22 is drawn through, for example, human head hair, said hair will be divided into narrow strands in the intermediate spaces 25 between the tines 22.

In a preferred embodiment, two current conduction means 26, 27 are located in the apparatus body 21, the cores 23 of the tines 22 being connected to said current conduction means in two groups in each case parallel to one another. In a preferred embodiment, each second tine 22 is connected to the current conduction means 26, whereas the tines 22 respectively situated between said second tines are connected to the current conduction means 27. This results in adjacent tines 22 being connected to a different potential of the high-voltage source 8.

However, it is also possible to suitably form the groups in a different way. For example, to connect in each case two tines which are situated next to one another to the same current conduction means 26 and to connect in each case two tines on the left and on the right of these two tines 22 to the other current conduction means 27. It is also feasible to connect in each case two tines to one potential and the respectively adjacent tines to the other potential, with the result that an arrangement of 2-1-2-1 . . . lines is produced in succession, wherein the in each case two tines 22 are connected to the first current conduction means 26 and the in each case individual tine 21 is connected to the current conduction means 27. Further combinations of the connections are likewise feasible.

In these apparatuses, the cores 23 of the tines 22 form the electrodes which are each surrounded by the dielectrics 24, with the result that the flow of current between the electrodes 23 is impeded by the dielectrics 24.

The exemplary embodiments of FIGS. 10 and 11 in turn differ by the connections to the high-voltage source 8 according to FIG. 4 (cf. FIG. 10) and, respectively, FIG. 6 (cf. FIG. 11).

FIG. 12 shows a further connection option for an apparatus according to the invention which involves the cores 23, which form the electrodes, of the tines 22 all being connected to the same connection of the high-voltage source 8, preferably to the AC-voltage connection according to FIG. 6. In order to treat the hair, it is possible, in this case, for the support of the hair, that is to say, for example, a wig fabric or the skin of a living organism which supports the hair to be connected to a reference potential by a counterelectrode 28, wherein the reference potential is preferably ground.

In this case, the support of the hair or the hair which is connected to the support forms the counterelectrode 28 to the electrodes 23 of the treatment apparatus. An arrangement of this kind is also possible for a tongs-like treatment apparatus according to FIGS. 1 to 9 and can be advantageously used in specific applications.

Therefore, all the apparatuses illustrated in the drawing can be used to execute plasma treatment of the surface of hair, which is fixedly arranged on a support, in a simple manner.

The invention claimed is:

1. A hand-held or moveable apparatus for treating human or animal hair, comprising a tongs-like body having two levers with which a divided strand of hair can be grasped and guided between contact faces of the two levers, wherein said contact faces are situated opposite one another, and each of said contact faces is formed by a dielectric that covers a flat electrode, wherein said flat electrode is connectable to a high-voltage source and one of said flat electrodes can be supplied with a voltage that differs from a voltage supplied to another of said flat electrodes.

2. The apparatus as claimed in claim 1, wherein said flat electrodes are embedded in said dielectric.

3. A hand-held or moveable apparatus for treating human or animal hair, comprising a comb-like body having tines which run parallel to one another, wherein said tines are formed with a conductive core which is surrounded on all sides by a dielectric, and wherein said conductive cores of said tines are connectable alternately to different voltages of the high-voltage source in order to form a plasma between adjacent tines.

4. The apparatus as claimed in claim 3, wherein the dielectric which surrounds said conductive core is a cohesive integral layer.

5. A method for treating human or animal hair, wherein the hair is divided into strands; comprising the steps of
  subjecting divided strands to dielectric plasma treatment by an apparatus which is connected to a high-voltage source, and
  drawing the apparatus through the strands, wherein one of said electrodes is supplied with a voltage that differs from a voltage supplied to another of said electrodes.

6. The method as claimed in claim 5, wherein said divided strands are grasped between two flat electrodes which are arranged on contact faces of tongs-like levers of said apparatus to provide one dielectric on each of said contact faces, and said direction through said divided strands.

7. The method as claimed in claim 5, wherein said hair is divided into strands by means of a comb-like structure having tines which run parallel to one another, wherein each of said tines has a conductive core which is surrounded on all sides by a dielectric and said conductive cores form electrodes, and said electrodes are connected to a said high-voltage source.

8. The method of claim 5, wherein said human or animal hair is uncut or living hair.

9. The method of claim 5, wherein said human or animal hair is cut and fixedly arranged on a support.

* * * * *